(12) United States Patent
Hafenrichter et al.

(10) Patent No.: US 9,746,445 B2
(45) Date of Patent: Aug. 29, 2017

(54) APPARATUS FOR AUTOMATED NON-DESTRUCTIVE INSPECTION OF AIRFOIL-SHAPED BODIES

(71) Applicant: The Boeing Company, Chicago, IL (US)

(72) Inventors: Joseph L. Hafenrichter, Seattle, WA (US); Gary E. Georgeson, Tacoma, WA (US); William Joseph Tapia, Kapowsin, WA (US); Michael D. Fogarty, Auburn, WA (US)

(73) Assignee: The Boeing Company, Chicago, IL (US)

(*) Notice: Subject to any disclaimer, the term of this patent is extended or adjusted under 35 U.S.C. 154(b) by 420 days.

(21) Appl. No.: 13/863,415

(22) Filed: Apr. 16, 2013

(65) Prior Publication Data

US 2014/0305216 A1    Oct. 16, 2014

(51) Int. Cl.
| G01N 29/07 | (2006.01) |
| G01N 29/22 | (2006.01) |
| G01N 29/24 | (2006.01) |
| G01N 29/265 | (2006.01) |
| G10K 11/35 | (2006.01) |
| G10K 11/00 | (2006.01) |

(52) U.S. Cl.
CPC ........... *G01N 29/07* (2013.01); *G01N 29/265* (2013.01); *G01N 29/223* (2013.01); *G01N 29/225* (2013.01); *G01N 2291/106* (2013.01); *G01N 2291/2694* (2013.01); *G10K 11/004* (2013.01); *G10K 11/35* (2013.01); *G10K 11/352* (2013.01); *G10K 11/355* (2013.01)

(58) Field of Classification Search
CPC ................. G01N 2291/2694; G01N 29/07
See application file for complete search history.

(56) References Cited

U.S. PATENT DOCUMENTS

| 4,146,967 | A |   | 4/1979 | Rohner et al. |
| 5,007,291 | A | * | 4/1991 | Walters ............... G01N 29/043 226/176 |
| 5,031,458 | A |   | 7/1991 | Young et al. |
| 5,121,629 | A | * | 6/1992 | Alba ..................... G01N 15/02 73/602 |

(Continued)

FOREIGN PATENT DOCUMENTS

EP         0289207 A2 * 11/1988 ........... G01N 29/223

OTHER PUBLICATIONS

MAUS Overview; http://www.boeing.com/defense-space/support/maintenance/commercialimaus.html: 4 pages.

*Primary Examiner* — R. A. Smith
*Assistant Examiner* — Herbert K Roberts
(74) *Attorney, Agent, or Firm* — Ostrager Chong Flaherty & Broitman P.C.

(57) ABSTRACT

An automated blade crawler capable of scanning a multiplicity of non-destructive inspection sensors over a surface of an airfoil-shaped body such as a blade component. The blade crawler is movable in a spanwise direction, thereby enabling a sensor array to inspect the surface area on one or both sides of the blade component in one pass. The sensors concurrently output scan imaging data which is multiplexed, the multiplexed being transmitted (via an electrical cable or wirelessly) to data collection and display hardware at an operations control center.

25 Claims, 10 Drawing Sheets

(56) References Cited

U.S. PATENT DOCUMENTS

| | | | |
|---|---|---|---|
| 5,335,547 A * | 8/1994 | Nakajima | G01N 29/22 702/167 |
| 5,634,378 A * | 6/1997 | Burkhardt | G01B 17/00 74/500.5 |
| 5,698,787 A | 12/1997 | Parzuchowski et al. | |
| 5,814,731 A * | 9/1998 | Alexander | G01N 29/225 73/624 |
| 6,220,099 B1 * | 4/2001 | Marti | G01N 29/226 73/633 |
| 6,571,636 B1 * | 6/2003 | McWhorter | G01N 29/2493 73/636 |
| 6,584,847 B1 * | 7/2003 | Hirose | G01B 17/00 73/579 |
| 6,637,266 B1 * | 10/2003 | Froom | G01M 5/0016 73/583 |
| 6,792,808 B1 * | 9/2004 | Batzinger | G01N 29/11 73/602 |
| 6,829,959 B2 | 12/2004 | Gifford et al. | |
| 7,231,826 B2 | 6/2007 | Bossi et al. | |
| 7,240,556 B2 | 7/2007 | Georgeson et al. | |
| 7,249,512 B2 | 7/2007 | Kennedy et al. | |
| 7,315,609 B2 | 1/2008 | Safai et al. | |
| 7,337,673 B2 | 3/2008 | Kennedy et al. | |
| 7,562,593 B2 | 7/2009 | Engelbart et al. | |
| 7,617,732 B2 | 11/2009 | Bui et al. | |
| 7,640,811 B2 | 1/2010 | Kennedy et al. | |
| 7,698,947 B2 | 4/2010 | Sarr | |
| 8,347,746 B2 | 1/2013 | Hafenrichter et al. | |
| 8,573,076 B2 * | 11/2013 | Sarr | G01N 29/041 483/16 |
| 9,385,448 B2 * | 7/2016 | Bondurant | G01N 29/223 |
| 2004/0050166 A1 * | 3/2004 | Batzinger | G01N 29/069 73/614 |
| 2005/0000279 A1 * | 1/2005 | Yogeswaren | B06B 1/0622 73/152.58 |
| 2005/0145033 A1 * | 7/2005 | Bossi | G01N 29/225 73/620 |
| 2006/0042391 A1 * | 3/2006 | Georgeson | G01N 29/07 73/633 |
| 2006/0043303 A1 | 3/2006 | Safai et al. | |
| 2006/0243051 A1 * | 11/2006 | Bui | G01N 29/043 73/618 |
| 2007/0068286 A1 * | 3/2007 | Piper | G01N 29/225 73/866.5 |
| 2009/0038398 A1 | 2/2009 | Lavoie et al. | |
| 2009/0114023 A1 * | 5/2009 | Bao | G01N 29/075 73/600 |
| 2009/0133502 A1 * | 5/2009 | Gret | G01N 29/12 73/633 |
| 2009/0223293 A1 * | 9/2009 | Owens | B01D 46/0086 73/620 |
| 2011/0137588 A1 * | 6/2011 | Walker | G01N 29/07 702/56 |
| 2011/0178727 A1 * | 7/2011 | Hafenrichter | G01M 5/0016 702/38 |
| 2012/0218868 A1 * | 8/2012 | Kahn | G01N 29/265 367/99 |
| 2013/0030727 A1 * | 1/2013 | Zalameda | G01N 29/045 702/56 |
| 2013/0289766 A1 * | 10/2013 | Hafenrichter | B25J 9/02 700/245 |
| 2014/0182479 A1 * | 7/2014 | Hafenrichter | B64F 5/0018 105/30 |

\* cited by examiner

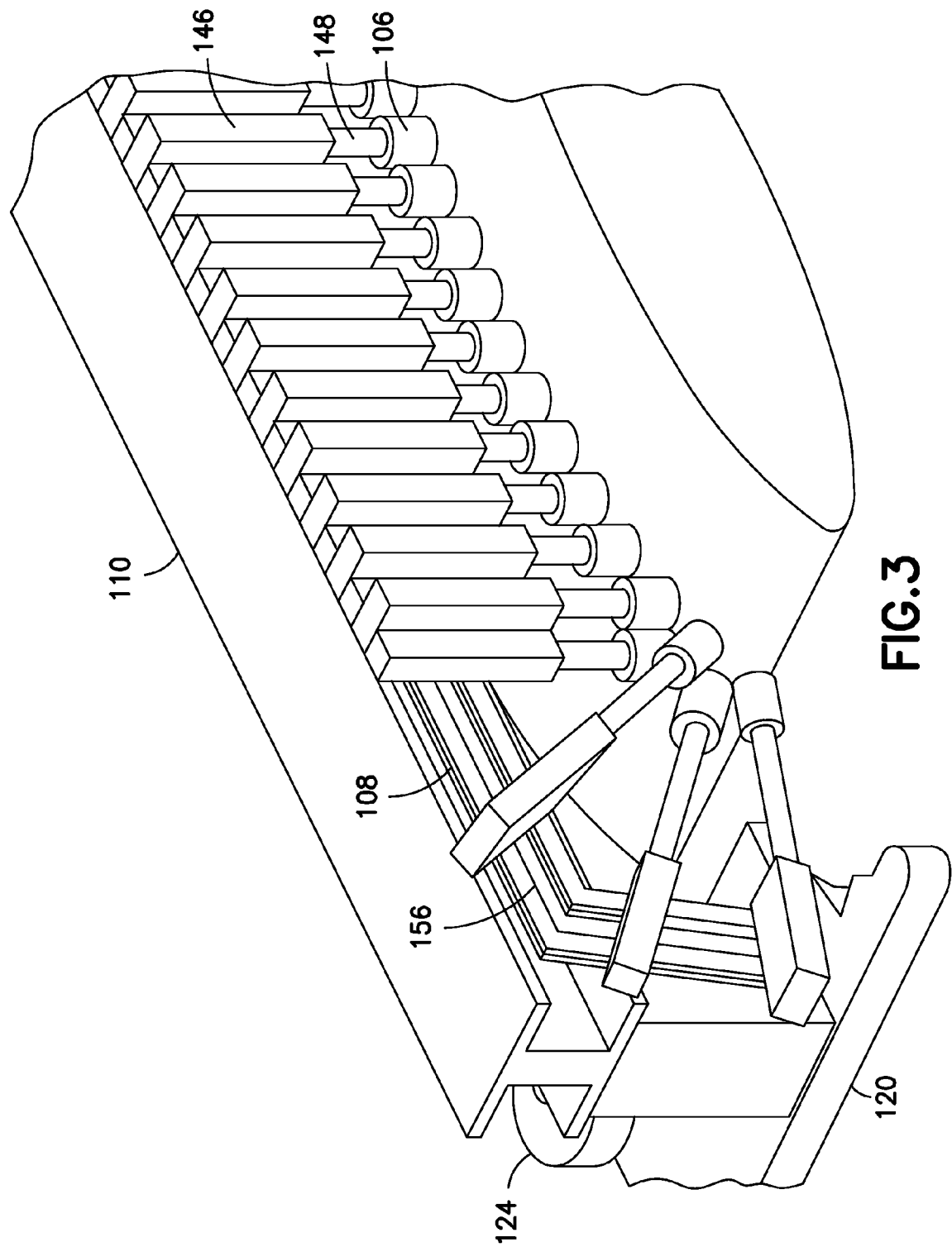

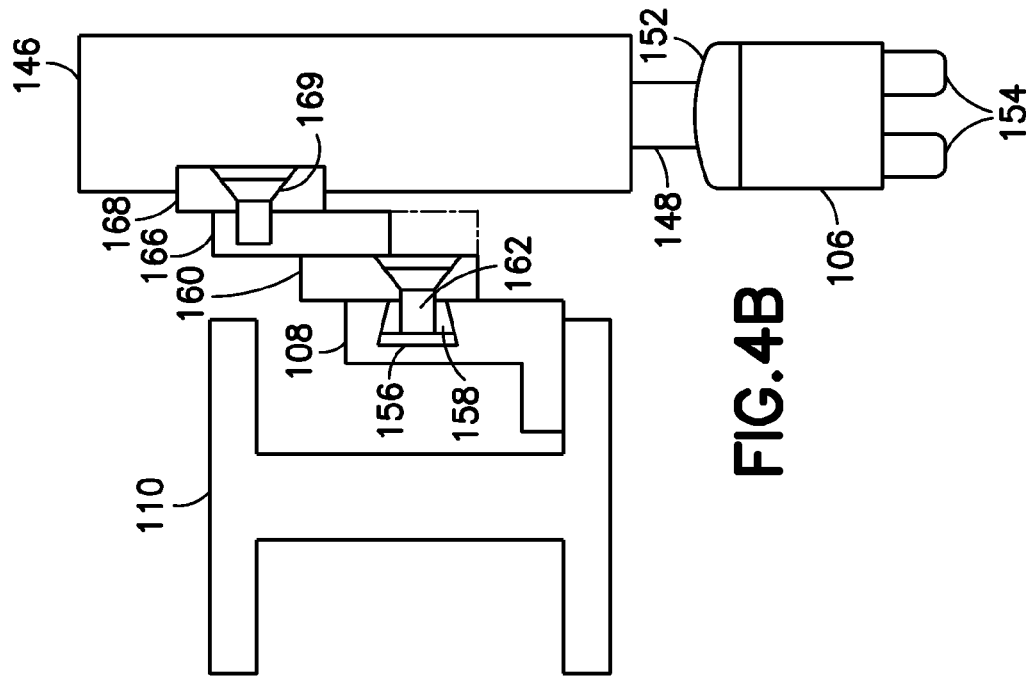
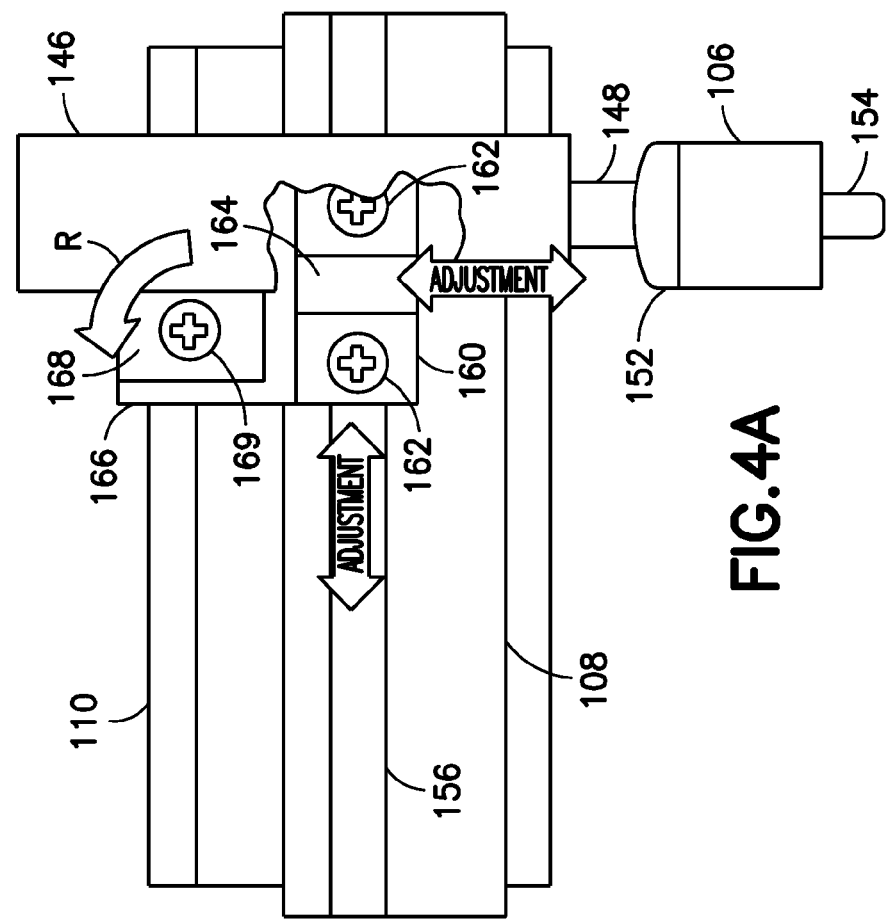
FIG. 4B
FIG. 4A

APPARATUS FOR AUTOMATED NON-DESTRUCTIVE INSPECTION OF AIRFOIL-SHAPED BODIES

BACKGROUND

The present disclosure relates generally to the field of automated non-destructive inspection (NDI) of aircraft structural elements such as airfoil-shaped bodies, and more particularly to an automated NDI scanning apparatus that is coupled to and travels along an airfoil-shaped body having a relatively short chord length, such as a rotorcraft blade, an aircraft propeller blade, a winglet, a projectile fin, an aircraft horizontal stabilizer, etc., while performing a NDI function.

In order to inspect airfoil-shaped bodies such as blade components, it is known to manually remove the blade components from the aircraft and then manually perform the inspection function. Removal of blade components from an aircraft is cost intensive. With helicopter blades, for example, the time spent removing, transporting, re-attaching, balancing and trimming the blades can be significant. Some helicopters require that the blades be removed and inspected every 50-75 flight hours, resulting in a dramatically reduced mission capability of the aircraft.

Furthermore, performing NDI functions manually generally calls for using skilled technicians. These technicians are in short supply; therefore the labor cost to manually perform NDI functions is significant. Because manual NDI is complex and repetitive, the likelihood of human error is high. When a repetitive NDI operation is not performed properly by a human, a flawed blade component could be reattached to the aircraft.

Surface-riding probes in gimbaled holders have been used in the non-destructive inspection of composite aerospace hardware in some gantry-type systems. Such gimbaled holders typically comprise two gimbals, one mounted on the other with orthogonal pivot axes to allow the gimbal-suspended sensor show to rotate with two degrees of freedom. These systems generally require some level of "teaching" of the scanner to get close enough to the contour, and the gimbaling of the shoe handles the difference. They are usually using pulse-echo ultrasound, so the sensor or riding shoe can rest directly on the surface. Besides requiring "teaching", these probes/shoes do not handle significant contours—like those on a rotorcraft blade leading edge—very well. One known scanning system has a spring-loaded shoe that works well for minor contours, but will not work for rotorcraft blades, particularly with sensors that have "contact feet" on them, because they tend to tip over.

Another apparatus for providing automated movement of a NDI sensor over a surface of an airfoil-shaped body is disclosed in U.S. Pat. No. 8,347,746. The apparatus in accordance with one embodiment comprises a "blade crawler" that travels in a spanwise direction along a rotorcraft blade. The blade crawler in turn has means for moving an NDI sensor in a chordwise direction. The respective movements in the spanwise and chordwise directions enable the NDI sensor to be rastered over the surface of the rotorcraft blade. The foregoing "blade crawler" automates what has been a slow and tedious hand-held inspection operation for rotorcraft blades, while allowing the rotorcraft blades to remain on the rotorcraft.

It would therefore be highly desirable to have an automated apparatus capable of scanning enabling a sensor array to inspect the entire surface area on one or both sides of an airfoil-shaped body in a single run along its length.

SUMMARY

The subject matter disclosed herein is an automated apparatus for performing NDI functions on airfoil-shaped bodies having short chord lengths, without the necessity of removing the airfoil-shaped body from the aircraft. There are a number of types of blade components on aircraft that will benefit from NDI automation, including helicopter blades, propeller blades, flaps, ailerons, trim tabs, slats, stabilators and stabilizers.

In accordance with embodiments disclosed hereinafter, the apparatus comprises an automated blade crawler capable of scanning a multiplicity of non-destructive inspection sensors (e.g., ultrasonic transducers) over a surface of an airfoil-shaped body such as a blade component. The blade crawler is movable in a spanwise direction, thereby enabling a sensor array to inspect the surface area on one or both sides of the blade component in one pass. The sensors concurrently output scan imaging data which is multiplexed, the multiplexed being transmitted (via an electrical cable or wirelessly) to data collection and display hardware at an operations control center.

In accordance with some embodiments, the blade crawler has an array of contact sensors which is movable in a spanwise direction over a contoured (i.e., non-planar) surface of an airfoil-shaped body. One side of the airfoil-shaped body can be inspected in one pass. Each contact sensor (e.g., of the pitch-catch type) is compliantly supported by mechanisms that allow the sensor to adjust its height and orientation in response to changes in inclination of the contacting portion of the contoured surface. The height and orientation-adjustment mechanisms maintain proper alignment and sufficient contact pressure while preventing sensor detachment due to tipping. It also provides means for damage prevention should the sensor hit an obstruction during spanwise travel. Alternatively, very light compression springs could be installed into the plungers, such that the plungers would not need to be computer controlled. Rather the plungers would simply keep the transducers in contact with the blade surface using simple spring force.

In accordance with other embodiments, the blade crawler has a dual array of non-contact sensors, which dual array is movable in a spanwise direction on opposing sides of an airfoil-shaped body. Both sides of the airfoil-shaped body can be inspected in one pass. Respective sets of non-contact sensors in each array can be operated in different modes, e.g., one set of sensors operate in a pitch-catch mode where the airfoil-shaped body is hollow, while another set of sensors operate in a through-transmission mode where the airfoil-shaped body is not hollow.

One aspect of the subject matter disclosed herein is a blade crawler comprising: a chassis comprising forward and rearward body parts, an elongated support member spanning a space between the forward and rearward body parts, and a plurality of rolling elements; a multiplicity of probe support assemblies coupled to and distributed along the elongated support member; a multiplicity of inspection probes coupled to the multiplicity of probe support assemblies; and an actuator for driving rotation of at least one of the rolling elements. In cases where the inspection probes are of the non-contact variety, the chassis may comprise two elongated members carrying respective multiplicities of inspection probes which oppose each other.

Another aspect of the disclosed subject matter is a method for non-destructive inspection of an airfoil-shaped body, comprising: coupling an array of inspection probes to a chassis, the inspection probes being distributed along an axis of the chassis; mounting the chassis on the airfoil-shaped body with the chassis axis disposed in a chordwise direction and in a manner such that the mounted chassis is not movable in the chordwise direction; moving the chassis in a spanwise direction along the airfoil-shaped body; pulsing the inspection probes to transmit wave energy; and outputting signals from the inspection probes representing wave energy received by the inspection probes following the pulsing, wherein the inspection probes are arranged to scan at least a surface on one side of the airfoil-shaped body in one spanwise movement.

A further aspect is an apparatus for non-destructive inspection of an airfoil-shaped body, comprising: a chassis adapted to be mounted to and travel in a spanwise direction along the airfoil-shaped body without movement in a chordwise direction, the chassis comprising a plurality of rolling elements configured to roll in the spanwise direction when the chassis is mounted to the airfoil-shaped body and a first elongated support member extending in a chordwise direction, the first elongated support member being proximal to one side the airfoil-shaped body when the chassis is mounted to the airfoil-shaped body; a multiplicity of probe support assemblies coupled to and distributed along the first elongated support member; a multiplicity of inspection probes coupled to the probe support assemblies, the inspection probes being directed toward one side of the airfoil-shaped body; and an actuator for causing the chassis to move in the spanwise direction along the airfoil-shaped body. Each probe support assembly may further comprise means for urging the inspection probe into contact with a surface of the first side of the airfoil-shaped body, and a self-orienting gimbal that supports the inspection probe. In one implementation, the first multiplicity of inspection probes are arranged in two rows, the inspection probes in one row being staggered relative to the inspection probes in the other row. In other implementations, the inspection probes of the first multiplicity can be arranged in more than two rows. The apparatus may further comprise means for adjusting and then fixing the positions and orientations of the probe support assemblies, and/or a pulser/receiver unit and a multiplexer coupling the inspection probes to the pulser/receiver unit.

In accordance with another aspect, the chassis may comprise two elongated support members extending in the chordwise direction, respective multiplicities of probe support assemblies being coupled to and distributed along the two elongated support members, and respective multiplicities of inspection probes being coupled to the respective multiplicities of probe support assemblies, the respective multiplicities of inspection probes being directed toward opposite sides of the airfoil-shaped body. The apparatus may further comprise a computer system programmed to perform the following operations: activate the actuator to cause spanwise movement of the chassis; control some of the inspection probes to operate in a pitch-catch mode; and control other inspection probes to operate in a through-transmission mode. Optionally, the apparatus may comprise barriers arranged to prevent stray wave energy around the leading and trailing edges of the airfoil-shaped body.

In some embodiments, the inspection probes are designed to contact the surface being inspected; in other embodiments, the inspection probes are designed to not be in contact with the surface being inspected.

In one implementation, the probe support assemblies are extendable (i.e., deployable) and retractable, in which case the apparatus further comprises: inspection probe lift actuators which cause the probe support assemblies to extend or retract; and a computer system programmed to perform the following operations: (a) determine respective distances separating the inspection probes from a surface of the airfoil-shaped body; and (b) selectively activate the inspection probe lift actuators to adjust the distances separating the inspection probes from that surface.

Other aspects are disclosed and claimed below.

BRIEF DESCRIPTION OF THE DRAWINGS

FIG. 3 shows a portion of the isometric view presented in FIG. 2 on a magnified scale.

FIG. 4A is a front elevational view of a portion of a probe mount structure in accordance with one embodiment.

FIG. 4B is a side elevational view of a portion of a probe mount structure in accordance with the embodiment partly shown in FIG. 4A.

Reference will hereinafter be made to the drawings in which similar elements in different drawings bear the same reference numerals.

DETAILED DESCRIPTION

The subject matter disclosed in detail hereinafter is directed to an autonomous, self-propelled, expandable and adjustable apparatus for inspecting in-service airfoil-shaped structures such as rotorcraft blades, aircraft propellers, smaller winglets, and narrow tail sections for structural damage by crawling along the length of the airfoil-shaped structure (i.e., in a spanwise direction) using the structure itself as the track. The apparatus carries an array of NDI sensors (e.g., ultrasonic transducers) for scanning respective chordwise sections of the airfoil-shaped structure in sequence as the crawler is moved in a spanwise direction. The NDI sensor array acquires data representing the structural conditions found as the crawler scans the airfoil-shaped structure. Multiplexed pulser/receiver cards, and a controller within a computer with imaging software, can be electrically coupled to the crawler by means of a cable or wirelessly to collect, display, and store NDI data.

Figure 1:
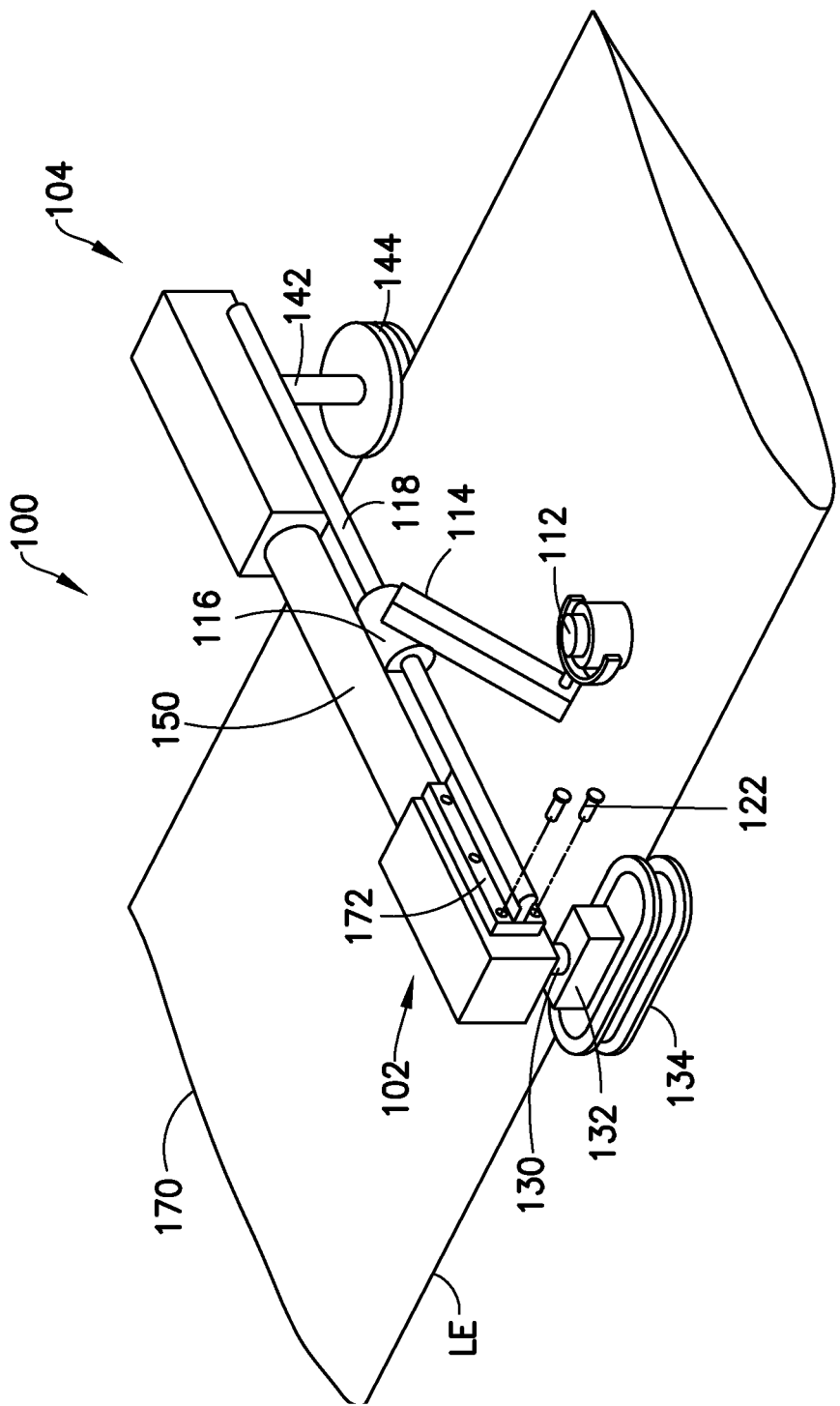
FIG. 1 is an isometric view of a blade crawler mounted on an airfoil structure having a short chord length and a significant contour, the blade crawler being movable in a spanwise direction and carrying a pitch-catch sensor which can be rastered in a chordwise direction.

To better appreciate the benefits provided by a blade crawler that carries an array of NDI sensors as compared to a blade crawler which carries a single NDI sensor, one implementation of a blade crawler of the latter type will now be described with reference to FIG. 1. It should also be appreciated that certain components (e.g., the means for driving spanwise travel of the crawler and the means for encoding the spanwise position of the crawler) shown in FIG. 1 are common to the crawlers described later with reference to FIGS. 2 and 6. (Means for driving spanwise travel and means for encoding spanwise position will not be shown in FIGS. 2 and 6.)

As seen in FIG. 1, a blade crawler 100 carrying a single NDI pitch-catch sensor 112, comprises a forward body part 102, a rearward body part 104, and an intercostal element 150 that interconnects the forward and rearward body parts to form a chassis. One of the forward and rearward body parts is displaceable along an axis of the intercostal element to facilitate adjustment of the distance separating the forward and rearward body parts, while the other body part is fixed relative to the intercostal element. For example, the intercostal element 150 may comprise a circular cylindrical tube or rod having one end fixed to the forward body part 102, while a portion extending from the other end has the rearward body part 104 slidably mounted thereon in the manner of a telescoping sleeve, allowing the distance between the forward and rearward body parts to be adjusted to adapt to airfoil-shaped bodies having different chord lengths.

The forward body part 102 is positioned near a forward (i.e., leading) edge of the airfoil-shaped body 170 that is to be inspected, and the rearward body part 104 is positioned near an opposing (i.e., trailing) edge of the structure to be inspected. Inspection of the airfoil-shaped body 170 is carried out, in part, by a pitch-catch sensor 112 pivotally mounted on one end of an arm 114, the other end of the arm 114 in turn being pivotably mounted to a slider 116 coupled to and slidable on a guide rod 118. (Alternatively, a guide rail or other guide element could be used in place of a guide rod.) The guide rod 118 is integrally formed with a mounting plate 172 that is fastened to the forward body part 102 by a plurality of fasteners 122.

The pitch-catch sensor 112 follows the curved surface of the airfoil-shaped body 170 when arm 114 exerts a normal force on the pivotably supported sensor 112. The normal force keeps the scanner in intimate contact with the airfoil surface, thus enabling the NDI functionality of the scanner. The normal force exerted by arm 114 can be generated by any conventional means, including the coupling of a spring, solenoid, pneumatic actuator or radial motion transducer (not shown in FIG. 1) between arm 114 and slider 116.

The forward body part 102 has a first rod 130 depending therefrom on which is mounted a control motor 132. A drive wheel (not shown) is operatively connected to and supported from the control motor 132, the latter causing a drive track 134 to circulate around the drive wheel and a second wheel (also not shown) while drive track 134 stays in frictional contact with the leading edge (LE in FIG. 1) of the airfoil-shaped body 170. Rotation of rod 130 causes the crawler 100 to travel in a spanwise direction provided that the drive track 134 does not slip relative to the leading edge.

Still referring to the system depicted in FIG. 1, a second rod 142 depends from the rearward body part and carries a follower encoder wheel 144 on the free end thereof. The spanwise position of crawler 100 is measured by a rotary encoder (incorporated in the rearward body part 104), which encodes rotation of encoder wheel 144. The encoder wheel 144 rides on the airfoil surface as the crawler travels in the spanwise direction. The rotary encoder sends an encoder pulse to the operations control center (e.g., via an encoder cable or a wireless connection) after each incremental movement of crawler 100 in the spanwise direction, which encoder pulses are used by a control computer and by ultrasonic pulser/receiver devices (not shown in FIG. 1) to determine the spanwise coordinate of each scan plane in a well-known manner.

The drive track 134 and the encoder wheel 144 are held against, and in frictional engagement with, the leading and trailing edges, respectively, of the airfoil-shaped body 170 to be inspected. This is accomplished by application of a tensile force imparted to the forward and rearward body parts 102, 104 (to be discussed below). The front and rearward body parts in turn (in response to the tensile force applied between the front and rearward body parts) apply a compressive force on the blade component (via the drive track 134 and encoder wheel 144) that holds the crawler on the blade component. Preferably, drive track 134 is made of a material that frictionally engages the leading edge of the structural part being inspected so as to impart a driving force that moves the crawler 100 spanwise along the airfoil-shaped body 170. Additionally, the encoder wheel 144 tracks the spanwise position of the crawler 100 as it translates along the airfoil-shaped body 170.

The rearward body part 104 carries encoder wheel 144, which depends from, and is attached to, the rearward body part on a telescoping rod 142 that allows the vertical position of the encoder wheel to be adjusted to fit the trailing edge of the airfoil-shaped body 170. The drive track 134 and encoder wheel 144, in conjunction, exert a gripping force on the airfoil-shaped body 170 that holds the crawler 100 thereon. A sufficient gripping force is generated when the telescoping sleeve (i.e., the rearward body part 104) retracts, causing the drive track 134 to engage the leading edge and the encoder wheel 144 (which also functions as an alignment wheel) to engage the trailing edge. Any one of a multiplicity of known linear motion devices (not shown) can be employed to cause the rearward body part 104 to retract relative to the intercostal element 150, including the following: a solenoid, a piston, a rack and pinion assembly, a spring, or other translation mechanism. For example, the gripping force can be generated by a spring which extends between the intercostal element 150 and the rearward body part 104. In accordance with one embodiment, the spring has opposing ends attached to (for applying a tensile force between) the rearward body part 104 and to one of a plurality of attachment points spaced along the length of the intercostal element 150. The spring may extend between an attachment point (not shown) on the intercostal element 150 and an attachment point (not shown) on the movable rearward body part 104. Multiple attachment points can be provided on the intercostal element 150 so that a spring tension within desired operational limits can be maintained during respective inspections of blades having different chord lengths. When one end of the tension spring is unlooked from a current attachment point, the rearward body part 104 can be translated along the intercostal element 150 in either direction and then the tension spring can be hooked onto a new attachment point, selected to produce a desired spring tension. In this manner, the crawler 100 can be expanded or retracted to accommodate structural elements having a range of chord lengths.

The drive track 134 shown in FIG. 1 can be replaced by a drive roller operatively coupled to the control motor 132 (carried by forward body part 102) and a secondary follower wheel displaced spanwise from the drive wheel (also carried by forward body part 102).

In accordance with the improvements disclosed herein, blade crawlers are designed to carry an array of NDI sensors that scan one or both surfaces of an airfoil-shaped body (e.g., from a blade root to a blade tip) in a single spanwise excursion. Such an arrangement reduces the time for automated NDI of an airfoil-shaped body as compared to the time when using a blade crawler that rasters a single sensor over the entire surface area.

Figure 2:
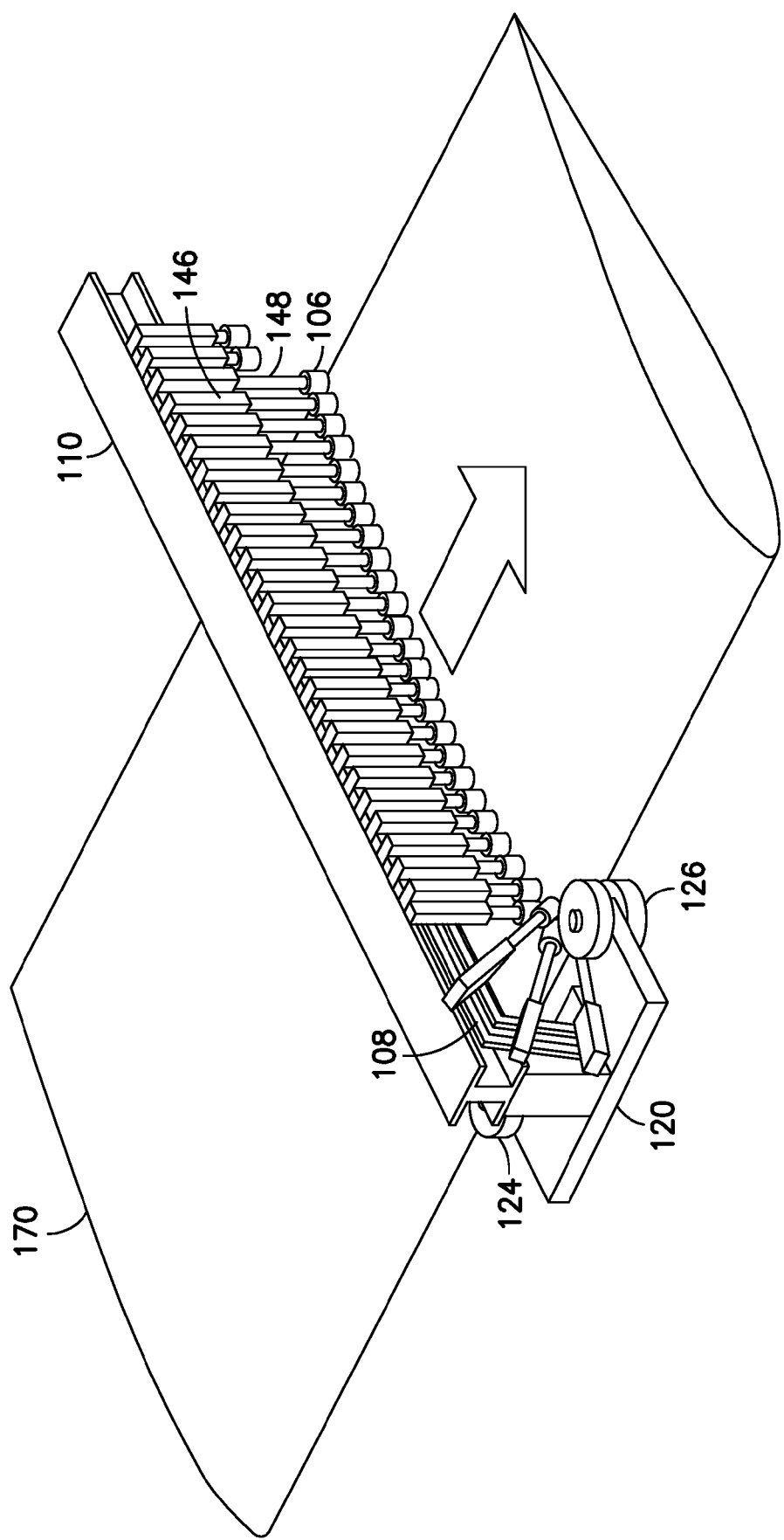
FIG. 2 is an isometric view of a blade crawler mounted on an airfoil structure having a short chord length and a significant contour, the blade crawler being movable in a spanwise direction and carrying an array of contact NDI sensors which can scan a surface of the airfoil structure in a single pass.

FIG. 2 shows components of a blade crawler that comprises a spanwise-movable chassis supporting a staggered array of floating low-frequency pitch-catch sensors 106. More specifically, the staggered array comprises two rows of sensors, one staggered relative to the other, both sensor rows extending in a chordwise direction when the blade crawler is mounted on an airfoil-shaped body 170. The chassis is designed to travel along the length of the airfoil-shaped body 170 in a spanwise direction indicated by the arrow in FIG. 2. The staggering of the sensors allows for full coverage of the blade area in a single pass.

In accordance with the embodiment shown in FIG. 2, the chassis may comprise a forward body part 120, a rearward body part (not shown), and an intercostal element 110 that interconnects the forward and rearward body parts. For example, the intercostal element 110 may comprise a rigid I-beam that is oriented in a chordwise direction and movable in a spanwise direction. The pitch-catch sensors 106 are coupled to a mounting rail 108, which is attached to or integrally formed with the intercostal element 110. The forward body part 120 is positioned near a forward (i.e., leading) edge of the airfoil-shaped body 170; the rearward body part (not shown) is positioned near an opposing (i.e., trailing) edge of that body. The rearward body part can be movable along the length of intercostal element 110 to adjust the chassis to fit on blades of different chord lengths. For the sake of simplicity, the means for exerting a gripping force on the airfoil structure and the means for moving the chassis in a spanwise direction are not shown in FIG. 2, but those means may comprise mechanisms similar to those depicted in FIG. 1.

Still referring to FIG. 2, the chassis may further comprise a drive wheel 124 and a follower wheel 126, both pivotably mounted to the forward body part 120, and a follower encoder wheel (not shown, but see item 144 in FIG. 1) mounted on the distal end of a shaft (not shown) which is pivotably coupled to the rearward body part (not shown). Alternatively, the follower encoder wheel may be replaced by a follower wheel, while an encoder wheel is mounted in a manner such that it outputs pulses indicating incremental spanwise movement of the crawler. The drive wheel 124 may be driven by a motor (not shown). The rotary encoder sends an encoder pulse to the operations control center (e.g., via an encoder cable or a wireless connection) after each incremental movement of the crawler in the spanwise direction, which encoder pulses are used by the control computer and by ultrasonic pulser/receiver devices to determine the spanwise position of each scan plane in a well-known manner.

Each pitch-catch sensor 106 is coupled to mounting rail 108 by means of a respective probe support assembly. As used herein, the term "probe" means a device comprising a sensor (e.g., an ultrasonic transducer) and a shoe in which the sensor is held. Each probe support assembly comprises a pneumatic or spring-loaded plunger mechanism 146 and a plunger shaft 148 slidably coupled to the plunger mechanism 146. Each plunger mechanism 146 is coupled to the mounting rail 108 by means of a respective adjustable mechanism which allows the position and orientation of each sensor 106 to be adjusted to ensure that the sensor array conforms to the shape of the contoured surface being inspected, including its leading edge. In the application depicted in FIG. 2, the mounting rail 108 carries more sensors 106 than are used for the particular chord length depicted in FIG. 2. Sensors disposed beyond the trailing edge of the airfoil-shaped body 170 are not needed and are shown in their retracted positions. For an airfoil-shaped body having a greater chord length than what is shown in FIG. 2, those sensors can be moved from their retracted to extended positions where they will contact the contoured surface of the airfoil-shaped body.

After the position and orientation of each sensor have been adjusted, during scanning the plunger mechanism 146 exerts a force (e.g., spring tension or air pressure) that urges the pitch-catch sensor 106 into contact with the opposing surface of the airfoil-shaped body 170. As the pitch-catch sensors 106 ride on the contoured surface of the airfoil-shaped body 170 (directly or with a stand-off spacer that keeps the sensors at a distance from the surface), a small spring tension or air pressure urges the plunger shaft 148 toward the surface. Preferably the plunger mechanisms 146 are coupled to the mounting rail 108 with positions and orientations that are selected, in conjunction with self-orienting gimbals described below and the extendable/retractable plunger shafts 148, to allow the sensors 106 to adjust their positions to compensate for changes in contour in the spanwise direction, thereby maintaining contact between the contact feet (i.e., tips) of each pitch-catch sensor and the contoured surface.

FIG. 3 shows a portion of the isometric view presented in FIG. 2 on a magnified scale. In this implementation, the mounting rail 108 has a dog-leg shape which, in conjunction with a respective adjustment mechanism, allow the positions and orientations of respective pitch-catch sensors 106 near the leading edge of the airfoil-shaped body 170 to be adjusted (i.e., by adjusting the position and orientation of the associated plunger mechanism 148) to enable inspection of the upper surface of that leading edge. (The bottom surface of the leading edge can be inspected during a second pass with the blade crawler in an inverted position.) In the alternative, the mounting rail could be curved near the leading edge of the airfoil-shaped body 170 instead of having a dog-leg shape.

In accordance with the arrangement depicted in FIGS. 2 and 3, one side of the airfoil-shaped body 170 can be inspected in one spanwise excursion by the array of pitch-catch sensors 106, which are arranged to cover the full width of the airfoil-shaped body. The other side can be inspected in a second pass after the position of the blade crawler has been inverted, in which case the array of pitch-catch sensors 106 will be aimed at the other side of airfoil-shaped body 170.

A mechanism for enabling manual adjustment of the position and orientation of each plunger mechanism 148 is shown in FIGS. 4A and 4B. As previously noted, each probe support assembly comprises a respective plunger mechanism 146 and a respective plunger shaft 148. As seen in the implementation depicted in FIGS. 4A and 4B, each probe support assembly further comprises a self-orienting gimbal 152. Each pitch-catch sensor 106 is coupled to a distal end of a respective plunger shaft 148 by means of a respective self-orienting gimbal 152. In addition, each pitch-catch sensor 106 comprises a pair of contact feet 154, ultrasonic wave energy being transmitted via one contact foot and received via the other contact foot.

Referring to FIG. 4A, the mounting rail 108 can be fastened to the intercostal element 110. The mounting rail 108 comprises a rail keyway 156. As seen in FIG. 4B, the rail keyway 156 may have a trapezoidal profile with the base of the trapezoid being located inside the mounting rail. The plunger mechanism 146 is coupled to the mounting rail 108 by means of an adjustment mechanism which comprises: (1) a pair of keyway nuts 158 (only one keyway nut is visible in FIG. 4B) which are seated inside the rail keyway 156; (2) a first slider plate 160 comprising a slider keyway 164, the first slider plate 160 being coupled to the mounting rail 108 by means of a pair of screws 162 which threadably engage the respective keyway nuts 158 installed in the rail keyway 156; (3) a second slider plate 166 which has a rail (not shown) that fits inside the slider keyway 164 of the first slider plate (a screw which fixes the position of the second slider plate 166 relative to the first slider plate 160 is not shown to avoid clutter in the drawing); (4) and a plunger swivel plate 168 which is fastened to the second slider plate 166 by means of a pivot screw 169. The plunger mechanism 146 is attached to or integrally formed with the plunger swivel plate 168.

To adjust the position and orientation of a plunger mechanism 146 relative to the mounting plate 108, the following adjustment procedure may be followed. For purposes of the following discussion, it will be assumed that the rail keyway 156 is horizontal and the slider keyway 164 is vertical. First, while screws 162 are in untightened states (meaning that the keyway nuts 158 are able to slide along the rail keyway 156), the first slider plate 160 is moved horizontally along the rail keyway 156 to a desired position and then screws 162 are tightened to fix the horizontal position of the first slider plate. Second, while the screw (not shown) which fixes the second slider plate 166 relative to the first slider plate 160 is in an untightened state, the second slider plate 166 is moved vertically along the slider keyway 164 to a desired elevation and than that same screw is tightened to fix the vertical position of the second slider plate 166. Third, while the pivot screw 169 is in an untightened state, the plunger swivel plate 168 is rotated to a desired angle and than the pivot screw 169 is tightened to fix the orientation of the plunger swivel plate 168 relative to the second slider plate 166. The result of this adjustment process is that the position and orientation of each plunger mechanism 146 can be adjusted and then fixed to ensure that each pitch-catch sensor 106 is urged (by the aforementioned pneumatic or spring means inside the plunger mechanism) into contact with the contoured surface of the airfoil-shaped body being inspected.

When multiple sensors are to be mounted in close proximity to the mounting rail, the sensors and their plunger mechanisms can be clustered in such a way that two or more plungers can utilize the same probe mounting mechanism. Alternatively, narrow-profile sliders with stacked mounting and attachment fasteners may be employed to enable a suite of sensors mounted in close proximity. Other configurations of plungers and sliders could be similarly employed to enable a closely stacked or staggered group of sensors. For example, in order to mount two rows of pitch-catch sensors, one row being staggered relative to the other (as shown in FIG. 3), the slider plates 160, 166 of the adjustment mechanisms for the row of sensors furthest away from the mounting rail could be increased in depth, thereby moving some sensors further away from the mounting rail.

Adjustment mechanisms of the type described above enable adjustable quick-set rail mounting of the plunger mechanisms 146 along the mounting rail 108 to allow for complete coverage of the contour of the airfoil-shaped body. The mounting of each plunger mechanism 146 can be angled to address the leading edge contour, as seen in FIG. 3.

Each pneumatic or spring-loaded plunger mechanism 146 is designed to exert a force on the associated plunger shaft 148 that urges feet 154 of each sensor 106 into contact with the contoured surface of the airfoil-shaped body. The pneumatic or spring-loaded plunger mechanism 146 facilitates positioning of each pitch-catch sensor 106 onto a highly contoured surface by allowing a wide range of vertical motion.

In addition, the self-orienting gimbals 152 provide each sensor with minor tilting capability to ensure that the contact feet make good contact at all times during the scanning, even if the contour of the surface changes. The gimbal mechanism is spring-loaded to self-align, but allows rotation of the sensor so that both feet ride on the surface at all times.

In accordance with a further advantageous feature, a mechanism can be provided for release of the plunger mechanism from the mounting rail if a high load is produced, for example, if the associated sensor encounters an obstacle that the sensor cannot float over, thereby protecting the array from damage. The release can be produced by a spring or release clip attachment of each plunger mechanism to the adjustment mechanism (e.g., to the plunger swivel plate 168 shown in FIG. 4B) that releases under a pre-set torque.

As the blade crawler moves in a spanwise direction along the airfoil-shaped body, all active sensors of the array will acquire scan imaging data concurrently. Multiplexing of the sensors allows them to be rapidly and sequentially interrogated, with scan imaging data being received from each sensor and correlated with that sensor's position in the array and the spanwise position of the mounting rail (derived via positional encoding as previously described).

Figure 5:
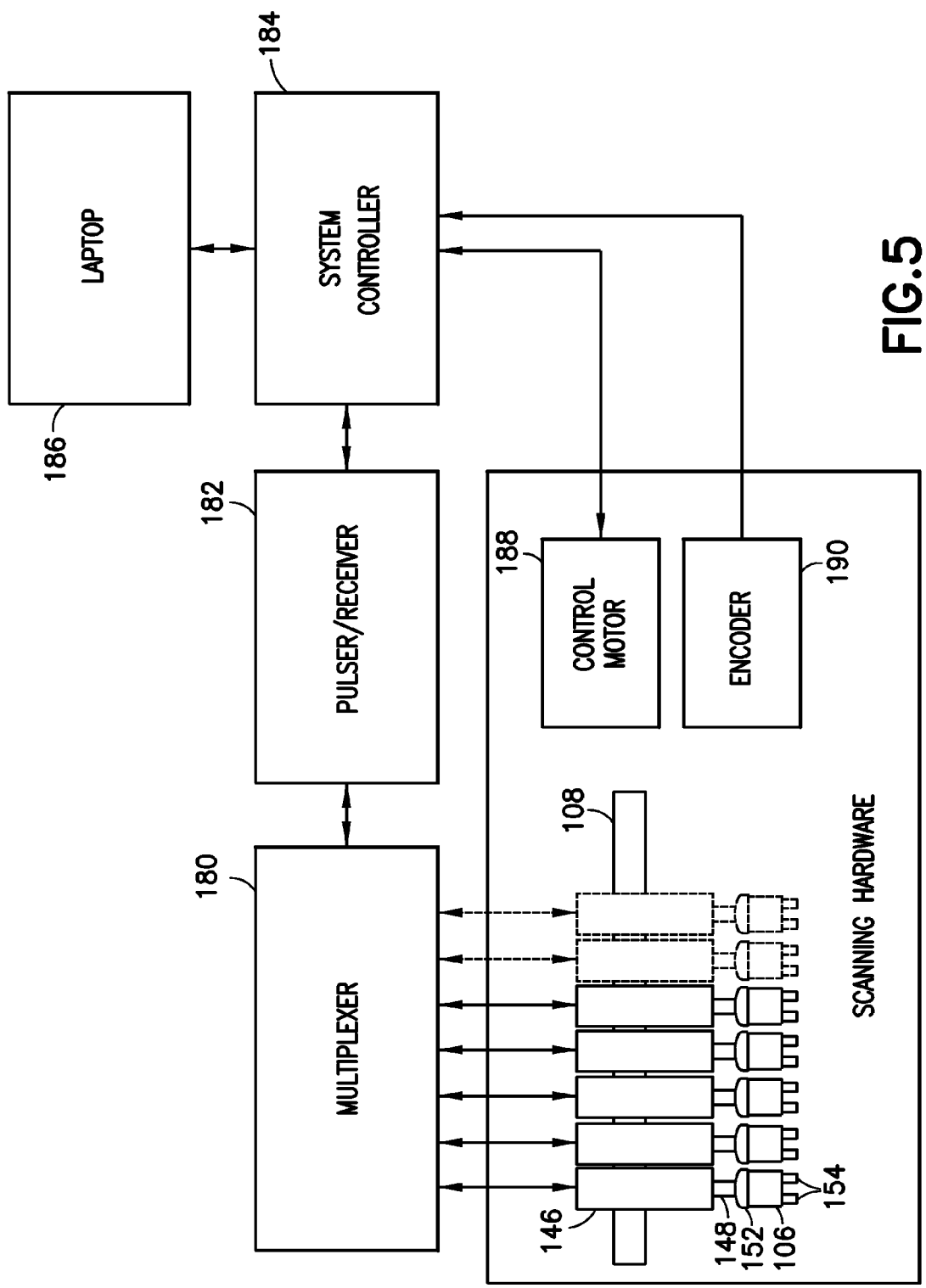
FIG. 5 is a block diagram showing components of a system for inspecting an airfoil-shaped body in accordance with one embodiment, such components including a multiplexer for sending concurrently acquired data in serial manner to a system controller.

FIG. 5 shows a system for inspecting an airfoil-shaped body in accordance with one embodiment. Spanwise movement of the mounting rail 108 (and sensor array) is driven by a motor 188 (e.g., a stepper motor or servo motor) which operates under the control of a system controller 184. As the mounting rail 108 is moved in the spanwise direction, a rotary encoder 190 sends encoder pulses representing incremental spanwise motion of the sensor array to the system controller 184. The pitch-catch sensors 106 are pulsed by the pulser of a pulser/receiver unit 182 via a multiplexer 180. The multiplexer 180 converts serial pulses into concurrent pulses for pulsing the sensors in unison. Ultrasonic wave energy returned from the part being inspected is transduced by the sensors 106 into electrical signals representing scan imaging data, which electrical signals are transmitted to the receiver of the pulser/receiver unit 182 via the multiplexer

180. The multiplexer 180 converts concurrently acquired scan imaging data into a serial format acceptable to the receiver of pulser/receiver unit 182. The pulser/receiver unit 182 sends the acquired scan imaging data to a NDI scan software application that runs on the system controller 184. The NDI scan software application correlates the acquired scan imaging data with respective spanwise positions of the sensor array. A laptop computer 186, connected to the system controller 184, provides a user interface for viewing scan images.

The system shown in FIG. 5 enables automated blade inspection in a reduced time by moving a full array of sensors along the length of a rotorcraft blade. However, this configuration can only inspect one side of the blade at a time. To inspect the other side, the blade crawler would be removed from the blade, inverted, and then mounted to the blade, depending from the blade in an upside-down position. The system shown in FIG. 5 also contemplates that the sensors run directly on (i.e., contact) the surface of the rotorcraft blade.

In accordance with a further improvement, a system can be provided which enables a rapid, non-contact method for inspection of a rotorcraft blade. An array of multiplexed airborne ultrasound transducers sends ultrasonic wave energy into the structure (sandwich, foam, laminate, etc.) from one side, which ultrasonic wave energy is sensed on the opposite side by a corresponding array of airborne ultrasonic transducers. When placed upon a motorized and positionally encoded blade crawler, this array can collect full-area C-scan data in a single pass.

Figure 6:
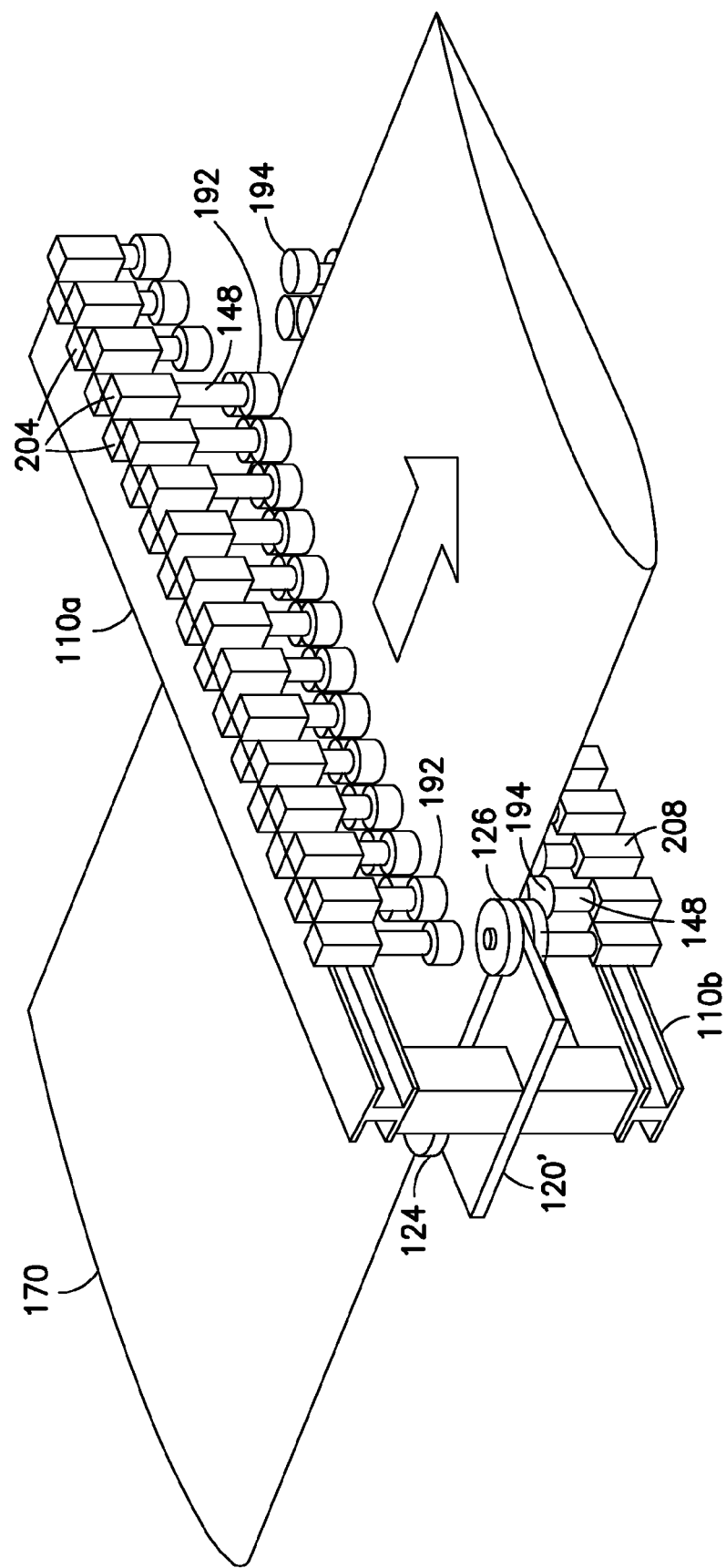
FIG. 6 is an isometric view of a blade crawler mounted on an airfoil structure having a short chord length and a significant contour, the blade crawler being movable in a spanwise direction and carrying a dual array of non-contact NDI sensors which can scan both sides of an airfoil structure in a single pass.

FIG. 6 shows components of a blade crawler that comprises a spanwise-movable chassis supporting respective arrays of sensors on opposing sides of an airfoil-shaped body 170. In the implementation shown in FIG. 6, the chassis supports one array of ultrasonic transducers 192 above (and not in contact) with the airfoil-shaped body 170 and another array of ultrasonic transducers 194 below (and not in contact) with the airfoil-shaped body 170. Both transducer arrays extend in a chordwise direction when the blade crawler is mounted on the airfoil-shaped body 170. The chassis is designed to travel along the length of the airfoil-shaped body 170 in a spanwise direction indicated by the arrow in FIG. 6. Each array may comprise two or more rows of transducers, each row being staggered with respect to the other, as previously described. The staggering of the sensors allows for full coverage of the airfoil-shaped body in a single pass.

In accordance with the embodiment shown in FIG. 6, the chassis may comprise a forward body part 120', a rearward body part (not shown), an upper intercostal element 110a that interconnects the forward and rearward body parts, and a lower intercostal element 110b that interconnects the forward and rearward body parts. For example, each intercostal element 110a,b may comprise a respective rigid I-beam. Ultrasonic transducers 192 are coupled to a first mounting rail (not shown) which is attached to or integrally formed with the intercostal element 110a, while ultrasonic transducers 194 are coupled to a second mounting rail (not shown) which is attached to or integrally formed with the intercostal element 110b. As previously described, the rearward body part can be movable along the lengths of intercostal elements 110a,b to adjust the chassis to fit on blades of different chord lengths. For the sake of simplicity, the means for exerting a gripping force on the airfoil structure and the means for moving the chassis in a spanwise direction are not shown in FIG. 6, but those means may comprise mechanisms similar to those depicted in FIG. 1.

Still referring to FIG. 6, the chassis may further comprise a drive wheel 124 and a follower wheel 126, both pivotably mounted to the forward body part 120', and a follower encoder wheel (not shown, but see item 144 in FIG. 1) mounted on the distal end of a shaft (not shown) which is pivotably coupled to the rearward body part (not shown). Alternatively, the follower encoder wheel may be replaced by a follower wheel, while an encoder wheel is mounted in a manner such that it outputs pulses indicating incremental spanwise movement of the crawler. The drive wheel 124 may be driven by a motor (not shown). The rotary encoder sends an encoder pulse to the operations control center (e.g., via an encoder cable or a wireless connection) after each incremental movement of the crawler in the spanwise direction, which encoder pulses are used by the control computer and by ultrasonic pulser/receiver devices to determine the spanwise position of each scan plane in a well-known manner.

The ultrasonic transducers 192, 194 are coupled to the mounting rails (not shown) by means of respective probe support assemblies. In accordance with one implementation, the probe support assemblies that support ultrasonic transducers 192 each comprise a respective plunger shaft 148 and a respective motorized plunger mechanism 204 which is activatable to raise or lower the respective plunger shaft, while the probe support assemblies that support ultrasonic transducers 194 each comprise a respective plunger shaft 148 and a respective plunger mechanism 208 which is manually adjustable, before starting an automated inspection procedure, to set the elevational position of the respective plunger shaft 148 relative to the plunger mechanism 208. In cases where the ultrasonic transducers are operated in a through-transmission mode, e.g., transducers 192 transmit while transducers 194 receive, the pairs of transmitting and receiving transducers are preferably aligned with each other, so that means for adjusting the orientation of the probe support assemblies are not needed. For example, all of the plunger mechanisms 204 can be mounted to intercostal element 110a in a parallel arrangement at the same elevation, while all of the plunger mechanisms 208 can be mounted to intercostal element 110b in a parallel arrangement at the same elevation. Then the elevational positions of the transducers can be adjusted by extending or retracting the associated plunger shafts 148.

Figure 7:
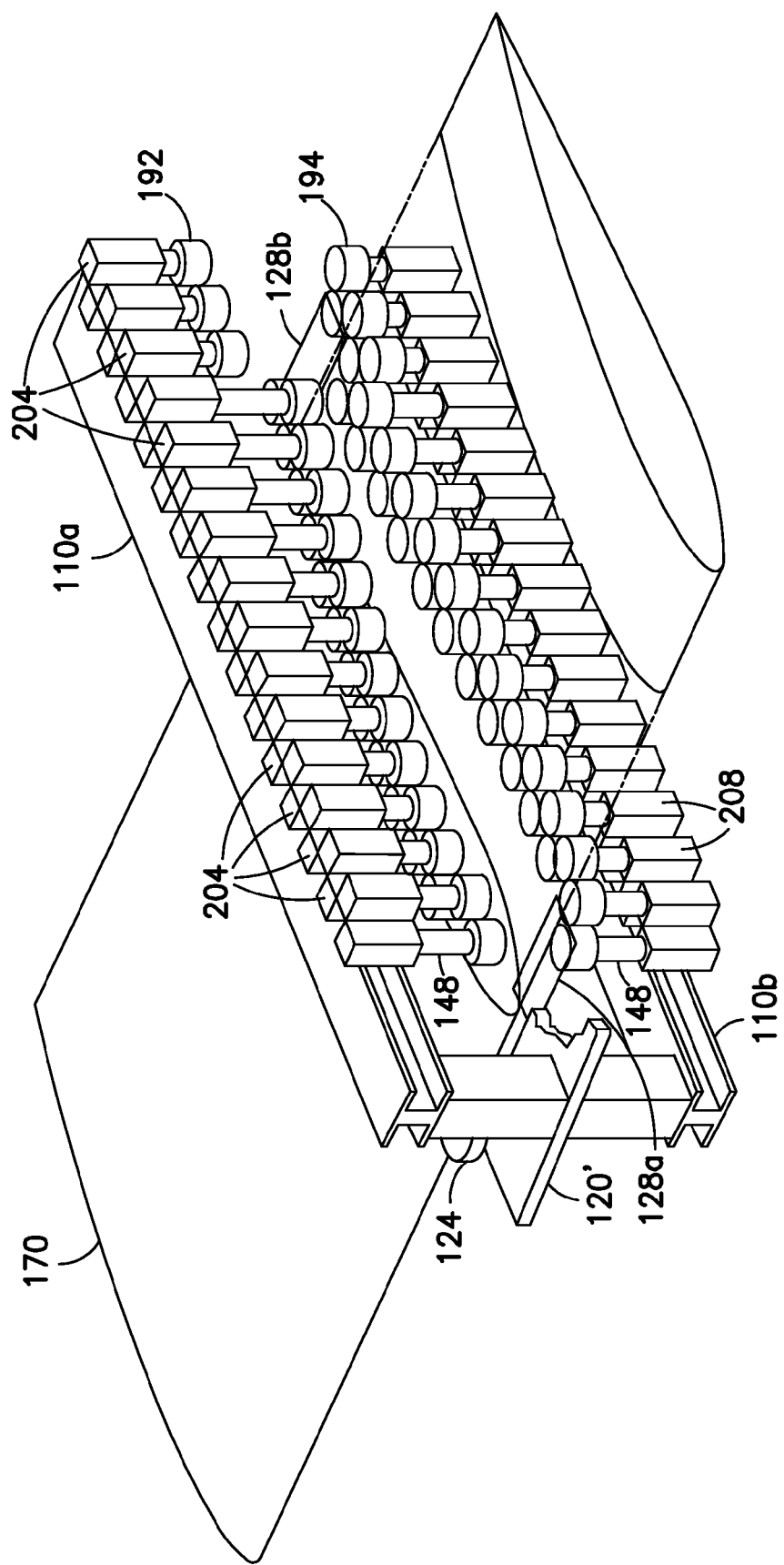
FIG. 7 is an isometric view of the same blade crawler shown in FIG. 6 with a portion of the airfoil structure removed to show the underlying sensor array.

FIG. 7 is an isometric view of the same blade crawler shown in FIG. 6 with a portion of the airfoil-shaped body 170 (and a portion of the forward body part 120') removed to show the underlying array of transducers 194. FIG. 7 further shows a forward ultrasonic barrier 128a which overlies the portion of the leading edge of the airfoil-shaped body 170 adjacent to the area being scanned and a rearward ultrasonic barrier 128b which overlies the portion of the trailing edge of the airfoil-shaped body 170 adjacent to the area being scanned. The forward ultrasonic barrier 128a may be attached to the forward body part 120', while the rearward ultrasonic barrier 128b may be attached to the rearward body part (not shown in FIG. 7). The ultrasonic barriers 128a,b at each edge prevent stray signals from traveling around the edge and interfering with the received signals of the transducers 194 near the edge.

Figure 8:
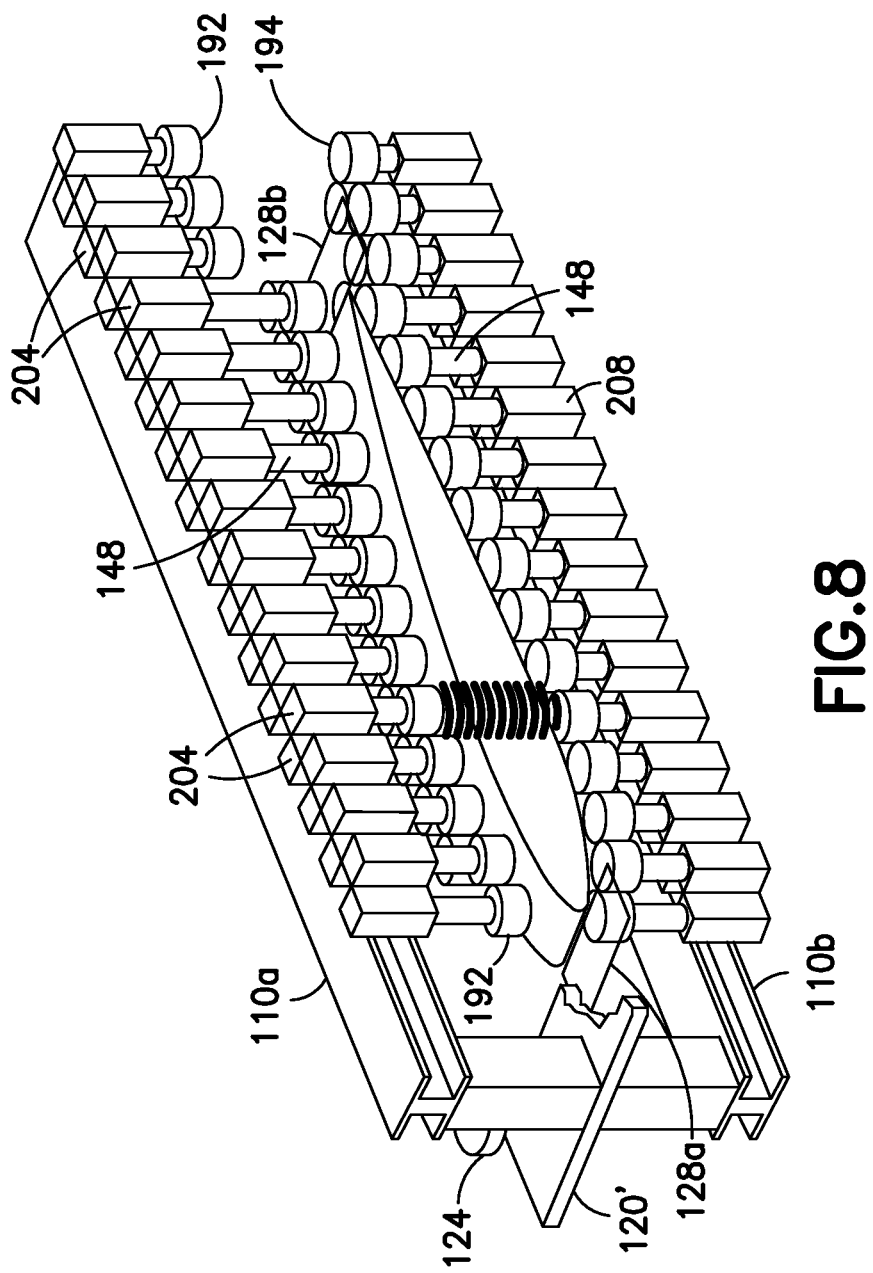
FIG. 8 is an isometric view of the same blade crawler shown in FIG. 6 with all but a portion of the airfoil structure removed, that portion being a non-hollow airfoil undergoing through-transmission ultrasonic inspection (transmitted acoustic waves are indicated by a series of spaced arcs).

FIG. 8 is an isometric view showing the blade crawler of FIG. 6 and only a portion of the airfoil-shaped structure 170 that is being scanned in a non-contact, through-transmission mode. FIG. 8 shows an ultrasonic transducer 192 transmitting acoustic waves (indicated by a series of spaced arcs) through a non-hollow portion of the airfoil-shaped body 170, which acoustic waves are being received by an opposing ultrasonic transducer 194. In the trough-transmission mode, the transmitted acoustic waves propagate through the airfoil-shaped body 170. Any defects in the airfoil-shaped body 170 located in the path of the propagating acoustic waves can be detected when transducer outputs are processed.

In accordance with a further feature of the system shown in FIGS. 6-8, some transducers can be operated in a through-transmission mode for scanning non-hollow portions of an airfoil-shaped body while other transducers are operated in a pitch-catch mode for scanning hollow portions of the same airfoil-shaped body. When operating in a through-transmission mode, electrical pulses from the pulser of a pulser/receiver unit to the transmitting transducers 192 and electrical signals produced by the receiving transducers 194 and sent to the receiver of the pulser/receiver unit in response to returned acoustic waves can be multiplexed by respective multiplexers to provide through-transmission ultrasound results across an entire non-hollow blade or across only non-hollow portions of a partially hollow blade. For hollow regions in the forward edge of some rotorcraft blades (no contiguous material across the blade), adjacent transducers on each side can be utilized in a single-sided pitch-catch mode of the generated structural wave. Transducers operating in a pitch-catch mode can also be connected to the pulser/receiver unit by means of multiplexers.

Figure 9:
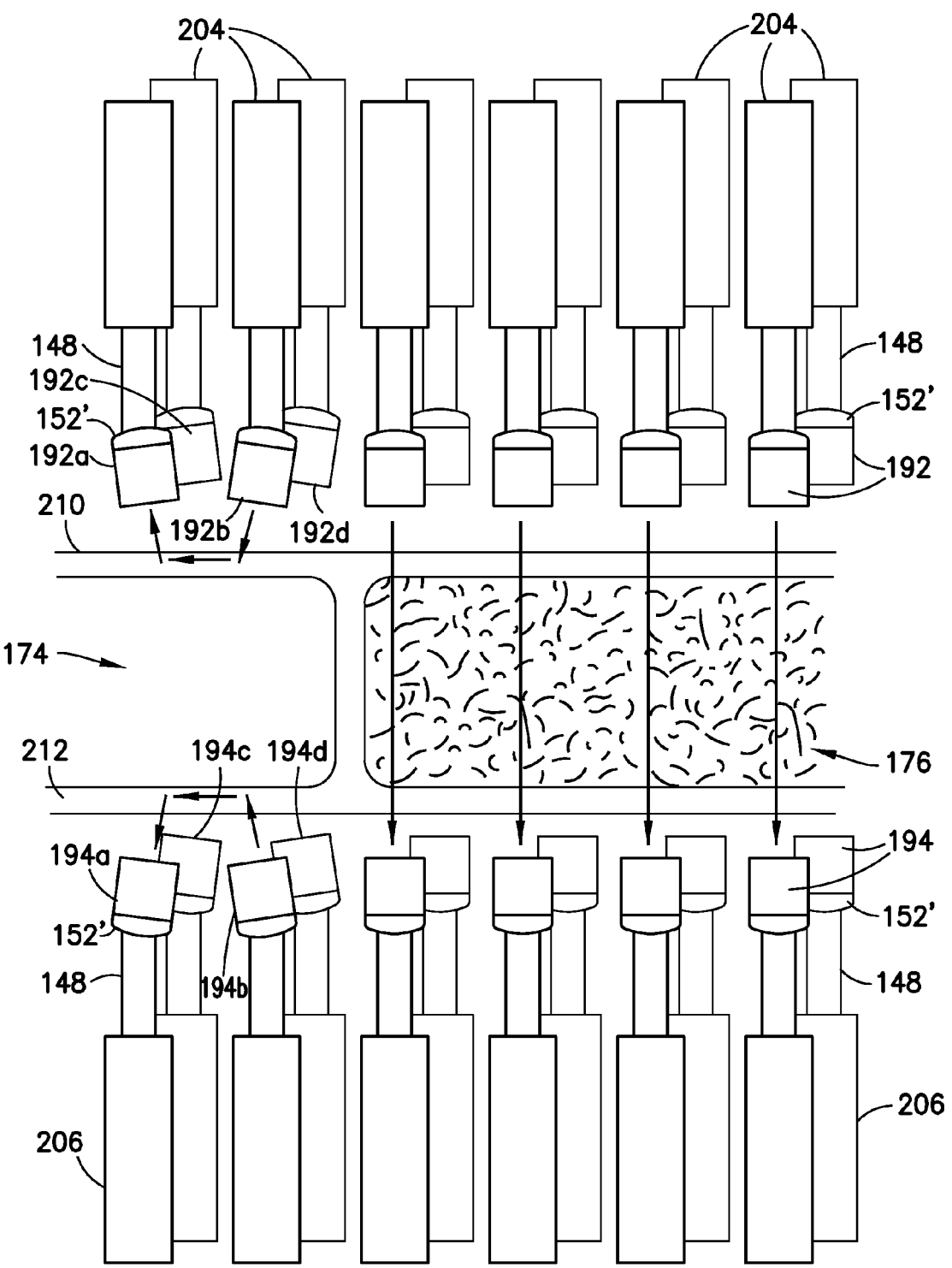
FIG. 9 is an elevational view showing a dual array of non-contact NDI sensors in accordance with one embodiment in which some sensors operate in a pitch-catch mode where the airfoil-shaped body is hollow, while other sensors operate in a through-transmission mode where the airfoil-shaped body is not hollow.

FIG. 9 shows a dual array of non-contact (i.e., airborne) ultrasonic transducers in accordance with one embodiment in which ultrasonic transducers 192*a-d* and 194*a-d* are being operated in a pitch-catch mode where the airfoil-shaped body is hollow, while other ultrasonic transducers 192, 194 operate in a through-transmission mode where the airfoil-shaped body is not hollow. In the example depicted in FIG. 9, the upper skin 210 of a hollow portion 174 is being scanned in a pitch-catch mode (indicated by a series of three arrows) by pairs of transducers 192*a*/192*b* and 192*c*/192*d*, while the lower skin 212 of hollow portion 174 is being scanned in a pitch-catch mode by pairs of transducers 194*a*/194*b* and 194*c*/194*d*. At the same time, transducers 192 are transmitting acoustic waves through a non-hollow portion 176 having a honeycomb or foam structure. The operation of some transducers in a pitch-catch mode enables NDI of hollow portions of an airfoil-shaped body where through-transmission is not possible (e.g., a hollow bullnose on some blades). Therefore, even for hollow-nosed rotorcraft blades, the entire blade can be inspected in one spanwise excursion.

In accordance with the embodiment depicted in FIG. 9, each transducer is coupled to an associated plunger shaft 148 by means of a respective settable gimbal 152'. The settable gimbals 152' enable the system operator to set the angles of any pair of adjacent transducers so that they can operate in a pitch-catch mode (as indicated by arrows in FIG. 9). Transducers that will operate in a through-transmission mode will have angles set at 0 degrees. Before an inspection process begins, the angles of the transducers can be set in accordance with the structure of the particular airfoil-shaped body to be inspected.

The gimbal setting mechanism may involve any one of a variety of processes. For example, the gimbals 152' can be manually set by a technician who manipulates the probe to the correct orientation; then the orientation is kept in place either by friction within the gimbal, or some mechanical means such as a set screw. Alternatively, the gimbals 152' could be set using an automated alignment mechanism such as a motorized or solenoid device that is guided by a contour detecting device such as a laser or sonic range finder. In accordance with a further alternative gimbal setting process, the correct orientation of the probe can be induced by bringing the contact feet of the probe into intimate contact with the part surface via the plunger mechanism; then the contact feet induce the gimbal to pivot until the pressures experienced by the contact feet are equalized. The resulting part surface angle is now transferred to the probe orientation. The probe is then retracted, while friction in the gimbal maintains this probe orientation throughout the inspection. Other methods are also possible.

An optional feature of the system shown in FIG. 6 is the automatic adjustment of the height of the transducers 192 relative to the surface of the airfoil-shaped body 170 by using the front surface reflection time of the transducer's ultrasonic signal to measure the distance. (This is not required for airborne ultrasonic transducers, but could be a benefit for image display or analysis.) A feedback control loop with a motorized lifter would adjust the height on the fly. That same signal can be used to balance the transducer amplitude levels.

Figure 10:
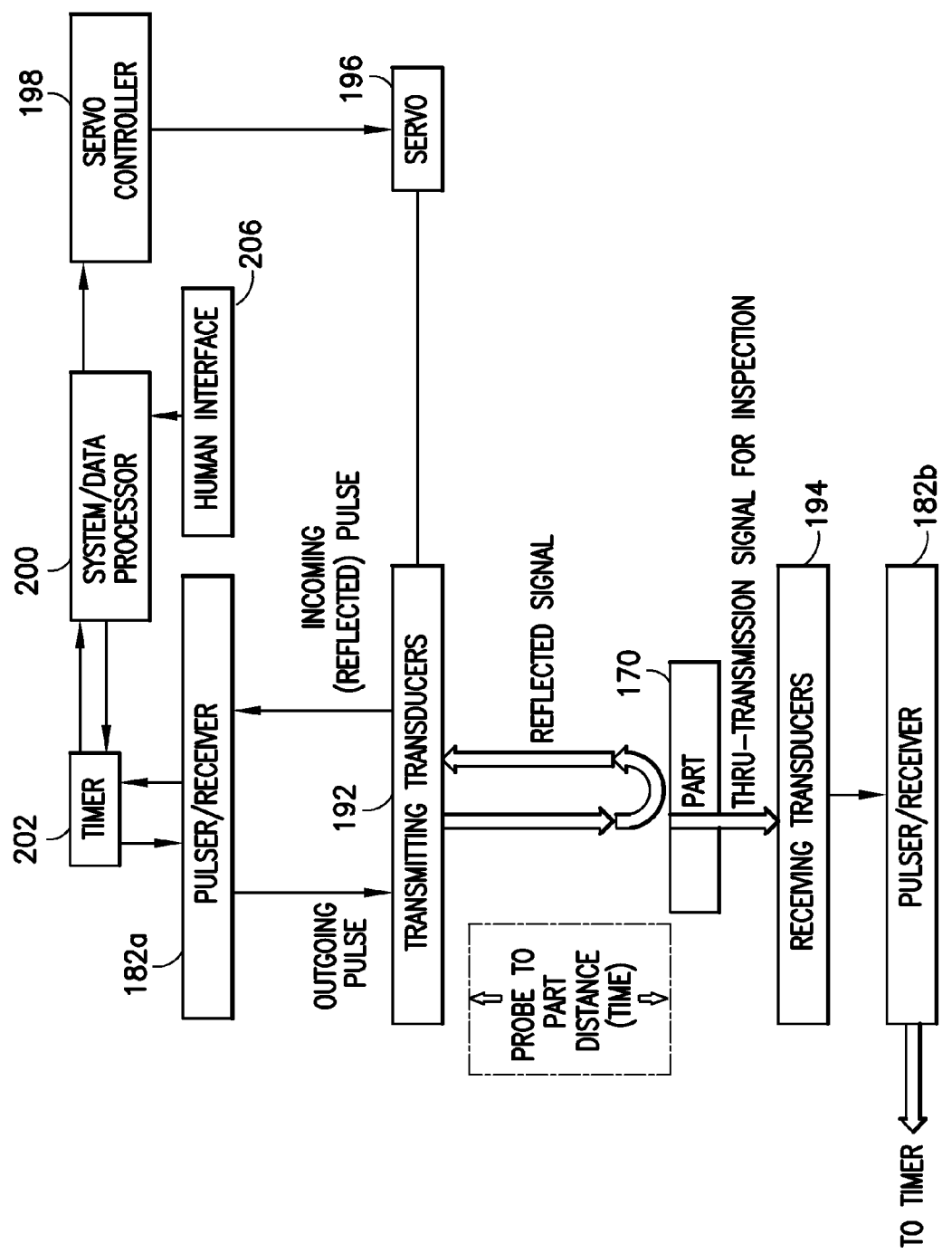
FIG. 10 is a block diagram showing components of a system for inspecting an airfoil-shaped body in accordance with another embodiment, including a feedback control loop with motorized lifters which adjust the heights of the sensors during scanning.

One embodiment of a system incorporating automatic transducer height adjustment is generally shown in FIG. 10. For the purposes of this schematic, only the automatic height adjustment of transducers operating in a through-transmission mode will be addressed. The system settings are entered into a system/data processor via a human interface 206. The settings would include a distance range that the probe will be held at. The system/data processor 200 will control a timer 202, which in turn controls the pulser/receiver unit 182*a*. The timer 202 commands the pulser of the pulser/receiver unit 182*a* to pulse, and then waits for a return signal. A voltage is sent from the pulser to a transmitting transducer 192, which transducer generates and emits an acoustic wave which propagates toward the portion of the air-foil shaped body 170 being inspected. The acoustic wave travels from the transmitting transducer to the surface of the air-foil shaped body 170 where some of the sound energy is transmitted into the part, and some reflected from the front (sound entry) surface. The reflected wave is received by the pulsed transducer and converted into a voltage that is detected by the receiver of the pulser/receiver unit 182*a*. This detected voltage is then sent through the timer 202 for measurement and then on to the system/data processor 200. If the measured sound travel time falls outside the prescribed range, the system/data processor 200 sends a command to the servo controller 198 to adjust accordingly by activating a servo motor 196 that is incorporated in the motorized plunger mechanism (item 204 in FIG. 6) that supports the pulsed transducer. This process can be repeated for each transducer to adjust their heights (i.e., the probe to part distance indicated in FIG. 10) individually to conform to the contour of the confronting chordwise portion of the surface of the airfoil-shaped body 170. When the heights of all of the transmitting transducers 192 have been adjusted, the system can be operated in an inspection mode wherein the receiving transducers 194 receive acoustic waves that have passed through the part being inspected and output corresponding voltages to the receiver of a pulser/receiver unit 182*b*.

One benefit of the systems shown in FIGS. 6-10 is a very rapid inspection method that does not require the sensors to contact the structure. If a rotorcraft blade is damaged so that there are breaks in the skin, current contact-type automated scanning would be limited by that damage. The system disclosed herein can scan over the top of any damage because of the headroom between the transducers and the structure. This system also does not require a second pass on the other side of the rotorcraft blade. If damage is found, the side of the damage can be determined by a quick check with a hand-held probe or (if it is in the laminate) by results of the pitch-catch mode for the transducers overlying the damage.

In accordance with the embodiments described above, a control computer is provided with information concerning the spanwise position of the chassis. This functionality can be provided by any one of a multiplicity of known positional tracking mechanisms. In accordance with various alternative embodiments, an optical tracking system can be used to determine the spanwise position of the chassis. For example, U.S. Pat. No. 7,643,893 discloses a motion capture system wherein multiple motion capture cameras are set up around the object to be scanned to create a three-dimensional capture volume that captures motion for all six degrees-of-freedom of the object being tracked. Alternatively, the optical tracking mechanism may comprise a local positioning system of the type disclosed in U.S. Pat. No. 8,044,991.

In accordance with other embodiments, the spanwise position of the blade crawler can be tracked using a light-emitting diode and a photodiode mounted to the crawler chassis in a relationship similar to what is incorporated in an optical computer mouse. This positional tracker uses an image sensor to image naturally occurring texture in the airfoil surface. Images of the surface are captured in continuous succession and compared with each other, using a process known as digital image correlation, to determine how far the crawler has moved.

In accordance with a further alternative, a capacitive linear encoder can be used to track the spanwise position of the crawler. Respective printed circuit boards of a capacitive linear encoder can be mounted on the crawler chassis and on a confronting surface of the airfoil-shaped body (the latter being removable) so that the printed circuit boards are capacitively coupled. As the crawler moves, the capacitance changes in a linear fashion and in a repeating manner. Alternatively, inductive or magnetic linear encoders can be used.

While automated blade crawlers have been described with reference to particular embodiments, it will be understood by those skilled in the art that various changes may be made and equivalents may be substituted for elements thereof without departing from the scope of the teachings herein. In addition, many modifications may be made to adapt a particular situation to the teachings herein without departing from the essential scope thereof. Therefore it is intended that the claims set forth hereinafter not be limited to the disclosed embodiments.

As used in the claims, the term "computer system" should be construed broadly to encompass a system having at least one computer or processor, and which may have multiple computers or processors that communicate through a network or bus. As used in the preceding sentence, the terms "computer" and "processor" both refer to devices having a processing unit (e.g., a central processing unit) and some form of memory (i.e., computer-readable medium) for storing a program which is readable by the processing unit.

The claims set forth hereinafter should not be construed to require that the steps or operations recited therein be performed in alphabetical order (alphabetical ordering in the claims is used solely for the purpose of referencing previously recited steps or operations) or in the order in which they are recited. Nor should they be construed to exclude any portions of two or more steps or operations being performed concurrently or alternatingly.

The invention claimed is:

1. A blade crawler comprising:
a chassis comprising forward and rearward body parts, a first elongated support member spanning a space between said forward and rearward body parts, and a plurality of rolling elements which are coupled to one or the other of said forward and rearward bodies and which enable said forward and rearward body parts to roll in a spanwise direction along a blade;
a first mounting rail attached to or integrally formed with said first elongated support member, said first mounting rail comprising a rail keyway comprising a straight groove defined by interior surfaces of said mounting rail;
a first multiplicity of adjustment mechanisms distributed at intervals along said first mounting rail, each of said first multiplicity of adjustment mechanisms comprising a respective pair of keyway nuts seated inside said rail keyway of said first mounting rail and in contact with said straight groove of said rail keyway;
a first multiplicity of probe support assemblies respectively attached to said first multiplicity of adjustment mechanisms, each of said first multiplicity of probe support assemblies comprising a respective self-orienting gimbal;
a first multiplicity of inspection probes respectively coupled to said respective self-orienting gimbals of said first multiplicity of probe support assemblies; and
an actuator for driving rotation of at least one of said rolling elements.

2. The blade crawler as recited in claim 1, wherein said probe support assemblies of said first multiplicity of probe support assemblies are configured so that said inspection probes of said first multiplicity of inspection probes are distributed alternatingly in first and second rows, the inspection probes of said second row being staggered relative to the inspection probes of said first row and being further away from said first elongated support member than are the inspection probes of said first row.

3. The blade crawler as recited in claim 1, wherein said chassis further comprises a second elongated support member spanning said space between said forward and rearward body parts, further comprising:
a second mounting rail attached to or integrally formed with said second elongated support member, said second mounting rail comprising a rail keyway;
a second multiplicity of adjustment mechanisms distributed at intervals along said second mounting rail, each of said second multiplicity of adjustment mechanisms comprising a respective pair of keyway nuts seated inside said rail keyway of said first mounting rail;
a second multiplicity of probe support assemblies respectively attached to said second multiplicity of adjustment mechanisms, each of said second multiplicity of probe support assemblies comprising a respective self-orienting gimbal; and
a second multiplicity of inspection probes respectively coupled to said respective self-orienting gimbals of said second multiplicity of probe support assemblies.

4. The blade crawler as recited in claim 3, wherein said first and second multiplicities of inspection probes are arranged so that inspection probes of said second multiplicity of inspection probes can receive wave energy transmitted by inspection probes of said first multiplicity of inspection probes.

5. The blade crawler as recited in claim 1, wherein each of said first multiplicity of adjustment mechanisms further comprises:

a pair of screws respectively threadably coupled to said pair of keyway nuts seated inside said first rail keyway;

a first slider plate comprising a slider keyway, said first slider plate being coupled to said first mounting rail by said pair of screws and said pair of keyway nuts; and a second slider plate comprising a rail which fits inside said slider keyway of said first slider plate.

6. The blade crawler as recited in claim 5, wherein each of said first multiplicity of adjustment mechanisms further comprises a plunger swivel plate that is fastened to said second slider plate, said plunger swivel plate being rotatable relative to said second slider plate when not fastened thereto and being attached to one of said first probe support assemblies.

7. The blade crawler as recited in claim 1, wherein said profile of said rail keyway is trapezoidal.

8. An apparatus for non-destructive inspection of an airfoil-shaped body, comprising:

a chassis adapted to be mounted to and travel in its entirety in a spanwise direction along the airfoil-shaped body without movement in a chordwise direction, said chassis comprising a plurality of rolling elements configured to roll in the spanwise direction when said chassis is mounted to the airfoil-shaped body and a first elongated support member extending in a chordwise direction, said first elongated support member being positioned adjacent to a first side of the airfoil-shaped body when said chassis is mounted to the airfoil-shaped body;

a first mounting rail attached to or integrally formed with said first elongated support member, said first mounting rail comprising a rail keyway comprising a straight groove defined by interior surfaces of said mounting rail;

a first multiplicity of adjustment mechanisms distributed at intervals along said first mounting rail, each of said first multiplicity of adjustment mechanisms comprising a respective pair of keyway nuts seated inside said rail keyway of said first mounting rail and in contact with said straight groove of said rail keyway;

a first multiplicity of probe support assemblies respectively attached to said first multiplicity of adjustment mechanisms, each of said first multiplicity of probe support assemblies comprising a respective self-orienting gimbal;

a first multiplicity of inspection probes respectively coupled to said respective self-orienting gimbals of said first multiplicity of probe support assemblies, said first multiplicity of inspection probes being directed toward the first side of the airfoil-shaped body; and an actuator for causing said chassis to move in the spanwise direction along the airfoil-shaped body.

9. The apparatus as recited in claim 8, wherein a probe support assembly of said first multiplicity of probe support assemblies comprises means for urging an inspection probe of said first multiplicity of inspection probes into contact with a surface of the first side of the airfoil-shaped body.

10. The apparatus as recited in claim 8, wherein said probe support assemblies of said first multiplicity of probe support assemblies are configured so that said inspection probes of said first multiplicity of inspection probes are distributed alternatingly in first and second rows, the inspection probes of said second row being staggered relative to the inspection probes of said first row and being further away from said first elongated support member than are the inspection probes of said first row.

11. The apparatus as recited in claim 8, wherein said inspection probes of said first multiplicity of inspection probes comprise pitch-catch sensors.

12. The apparatus as recited in claim 8, further comprising:

a pulser/receiver unit; and a multiplexer coupling said first multiplicity of inspection probes to said pulser/receiver unit.

13. The apparatus as recited in claim 8, wherein said chassis further comprises a second elongated support member extending in the chordwise direction, said second elongated support member being positioned adjacent to a second side the airfoil-shaped body when said chassis is mounted to the airfoil-shaped body, and wherein said apparatus further comprises:

a second mounting rail attached to or integrally formed with said second elongated support member, said second mounting rail comprising a rail keyway;

a second multiplicity of adjustment mechanisms distributed at intervals along said second mounting rail, each of said second multiplicity of adjustment mechanisms comprising a respective pair of keyway nuts seated inside said rail keyway of said first mounting rail;

a second multiplicity of probe support assemblies respectively attached to said second multiplicity of adjustment mechanisms, each of said second multiplicity of probe support assemblies comprising a respective self-orienting gimbal; and a second multiplicity of inspection probes respectively coupled to said respective self-orienting gimbals of said second multiplicity of probe support assemblies, said second multiplicity of inspection probes being directed toward the second side of the airfoil-shaped body.

14. The apparatus as recited in claim 13, further comprising a computer system programmed to perform the following operations:

activate said actuator to cause spanwise movement of said chassis;

control a first set of inspection probes belonging to said first multiplicity of inspection probes and a second set of inspection probes belonging to said second multiplicity of inspection probes to operate in a pitch-catch mode during said spanwise movement; and control a third set of inspection probes belonging to said first multiplicity of inspection probes and a fourth set of inspection probes belonging to said second multiplicity of inspection probes to operate in a through-transmission mode during said spanwise movement.

15. The apparatus as recited in claim 8, further comprising a barrier arranged to prevent stray wave energy around an edge of the airfoil-shaped body.

16. The apparatus as recited in claim 8, wherein said inspection probes of said first multiplicity of inspection probes do not contact a surface of the first side of the airfoil-shaped body when said chassis is mounted to the airfoil-shaped body.

17. The apparatus as recited in claim 8, wherein each of said first multiplicity of probe support assemblies is extendable and retractable, further comprising:

a multiplicity of inspection probe lift actuators coupled to said first multiplicity of probe support assemblies in a manner capable of causing said probe support assemblies to extend or retract; and a computer system programmed to perform the following operations:

(a) determine respective distances separating said inspection probes from a surface of the first side of the airfoil-shaped body; and (b) selectively activate said inspection probe lift actuators to adjust the distances separating said inspection probes from the surface of the first side of the airfoil-shaped body.

18. The apparatus as recited in claim 17, wherein operation (a) comprises timing travel times of ultrasound wave energy transmitted from said inspection probes toward the surface of the first side of the airfoil-shaped body and reflected back to and received by said inspection probes.

19. The apparatus as recited in claim 8, wherein each of said first multiplicity of adjustment mechanisms further comprises:
   a pair of screws respectively threadably coupled to said pair of keyway nuts seated inside said first rail keyway;
   a first slider plate comprising a slider keyway, said first slider plate being coupled to said first mounting rail by said pair of screws and said pair of keyway nuts; and
   a second slider plate comprising a rail which fits inside said slider keyway of said first slider plate.

20. The apparatus as recited in claim 19, wherein each of said first multiplicity of adjustment mechanisms further comprises a plunger swivel plate that is fastened to said second slider plate, said plunger swivel plate being rotatable relative to said second slider plate when not fastened thereto and being attached to one of said first probe support assemblies.

21. The apparatus as recited in claim 8, wherein said profile of said rail keyway is trapezoidal.

22. A method for non-destructive inspection of an airfoil-shaped body, comprising:
   attaching a mounting rail to or forming a mounting rail on an elongated support member of a chassis, the mounting rail comprising a rail keyway comprising a straight groove defined by interior surfaces of the mounting rail;
   independently affixing each one of a multiplicity of adjustment mechanisms to the mounting rail at respective positions so that the multiplicity of adjustment mechanisms are distributed and not movable in a direction parallel to the mounting rail using fasteners which are inserted in the rail keyway of the mounting rail and in contact with the straight groove of the rail keyway;
   independently affixing each of a multiplicity of probe support assemblies to a respective one of the multiplicity of adjustment mechanisms;
   coupling each one of a multiplicity of inspection probes to a respective one of the multiplicity of probe support assemblies;
   mounting the chassis on the airfoil-shaped body with the mounting rail disposed in a chordwise direction and in a manner such that the entire chassis is movable in a spanwise direction along the airfoil-shaped body and is not movable in a chordwise direction;
   moving the entire chassis in the spanwise direction along the airfoil-shaped body;
   pulsing the inspection probes to transmit wave energy; and
   outputting signals from the inspection probes representing wave energy received by the inspection probes following said pulsing,
   wherein the inspection probes are arranged to scan at least a surface on one side of the airfoil-shaped body in one spanwise movement.

23. The method as recited in claim 22, further comprising changing a distance separating the inspection probes from opposing portions of a surface on one side of the airfoil-shaped body to adjust for spanwise changes in contour of that surface.

24. The method as recited in claim 22, wherein some of the inspection probes are operated in a pitch-catch mode while other inspection probes are operated in a through-transmission mode.

25. The method as recited in claim 22, wherein the profile of the rail keyway is trapezoidal.

* * * * *